(12) United States Patent
Quick

(10) Patent No.: US 9,078,711 B2
(45) Date of Patent: Jul. 14, 2015

(54) DEVICES AND METHODS FOR DETECTION OF SLIPPAGE OF MAGNETIC COUPLING IN IMPLANTABLE MEDICAL DEVICES

(75) Inventor: Richard L. Quick, Mission Viejo, CA (US)

(73) Assignee: Ellipse Technologies, Inc., Aliso Viejo, CA (US)

(*) Notice: Subject to any disclaimer, the term of this patent is extended or adjusted under 35 U.S.C. 154(b) by 310 days.

(21) Appl. No.: 13/490,107

(22) Filed: Jun. 6, 2012

(65) Prior Publication Data

US 2013/0328553 A1 Dec. 12, 2013

(51) Int. Cl.
| G01B 7/14 | (2006.01) |
| A61B 17/72 | (2006.01) |
| A61B 17/70 | (2006.01) |
| A61B 19/00 | (2006.01) |

(52) U.S. Cl.
CPC ......... *A61B 17/7216* (2013.01); *A61B 17/7016* (2013.01); *A61B 2019/461* (2013.01)

(58) Field of Classification Search
USPC .................................................. 324/207.15
See application file for complete search history.

(56) References Cited

U.S. PATENT DOCUMENTS

| 3,512,901 A | 5/1970 | Law |
| 4,973,331 A | 11/1990 | Pursley et al. |
| 5,626,579 A | 5/1997 | Muschler et al. |
| 5,672,175 A | 9/1997 | Martin |
| 5,704,939 A | 1/1998 | Justin |
| 5,762,599 A | 6/1998 | Sohn |
| 5,961,553 A | 10/1999 | Coty et al. |
| 6,336,929 B1 | 1/2002 | Justin |
| 6,657,351 B2 | 12/2003 | Chen et al. |
| 6,667,725 B1 | 12/2003 | Simons et al. |
| 6,796,984 B2 | 9/2004 | Soubeiran |
| 6,835,207 B2 | 12/2004 | Zacouto et al. |
| 6,849,076 B2 | 2/2005 | Blunn et al. |
| 7,001,346 B2 | 2/2006 | White |

(Continued)

FOREIGN PATENT DOCUMENTS

| WO | WO 2006/090380 | 8/2006 |
| WO | WO 2006/103074 | 10/2006 |
| WO | WO 2013119528 A1 | 8/2013 |

OTHER PUBLICATIONS

Montague, R.G. et al., Magnetic Gear Dynamics for Servo Control, Department of Electronic and Electrical Engineering, The University of Sheffield, Mappin Street, Sheffield, S1 3JD, United Kingdom, pp. 1192-1197, IEEE (2010).

(Continued)

*Primary Examiner* — Jay Patidar
(74) *Attorney, Agent, or Firm* — Knobbe, Martens, Olson & Bear LLP

(57) ABSTRACT

A device for the detection of slippage of magnetic coupling between an implanted medical device having a magnet and an externally applied magnetic field includes at least one external magnet configured to apply the externally applied magnetic field, an induction coil disposed external to the subject and between the at least one external magnet and the implanted medical device, and a detection circuit operatively coupled to the induction coil and configured to detect slippage between the rotational orientation of the magnet of the implanted device and the externally applied magnetic field based at least in part on the varying frequency components of the voltage waveform across the induction coil.

19 Claims, 13 Drawing Sheets

(56) References Cited

U.S. PATENT DOCUMENTS

| | | |
|---|---|---|
| 7,135,022 B2 | 11/2006 | Kosashvili et al. |
| 7,862,502 B2 | 1/2011 | Pool et al. |
| 8,057,472 B2 | 11/2011 | Walker et al. |
| 2005/0055025 A1 | 3/2005 | Zacouto et al. |
| 2005/0080427 A1 | 4/2005 | Govari et al. |
| 2005/0234448 A1 | 10/2005 | McCarthy |
| 2005/0246020 A1 | 11/2005 | Southworth |
| 2005/0261779 A1 | 11/2005 | Meyer |
| 2006/0032314 A1 | 2/2006 | Hnat et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0052782 A1 | 3/2006 | Morgan et al. |
| 2006/0069447 A1 | 3/2006 | DiSilvestro et al. |
| 2006/0070451 A1 | 4/2006 | Walsh et al. |
| 2006/0136062 A1 | 6/2006 | DiNello et al. |
| 2007/0179493 A1 | 8/2007 | Kim |
| 2007/0276369 A1 | 11/2007 | Allard et al. |
| 2007/0276378 A1 | 11/2007 | Harrison et al. |
| 2008/0033436 A1 | 2/2008 | Song et al. |
| 2008/0097188 A1 | 4/2008 | Pool et al. |
| 2008/0097249 A1 | 4/2008 | Pool et al. |
| 2008/0097487 A1 | 4/2008 | Pool et al. |
| 2008/0097496 A1 | 4/2008 | Chang et al. |
| 2008/0172072 A1 | 7/2008 | Pool et al. |
| 2008/0300597 A1 | 12/2008 | Morgan et al. |
| 2009/0112207 A1 | 4/2009 | Walker et al. |
| 2009/0112262 A1 | 4/2009 | Pool et al. |
| 2009/0112263 A1 | 4/2009 | Pool et al. |
| 2009/0273353 A1 | 11/2009 | Kroh et al. |
| 2010/0094302 A1 | 4/2010 | Pool et al. |
| 2010/0217271 A1* | 8/2010 | Pool et al. ............ 606/90 |
| 2010/0228167 A1 | 9/2010 | Ilovich et al. |
| 2010/0262239 A1 | 10/2010 | Boyden et al. |
| 2010/0274114 A1 | 10/2010 | Denker et al. |
| 2011/0004076 A1 | 1/2011 | Janna et al. |
| 2011/0152725 A1 | 6/2011 | Demir et al. |
| 2011/0237861 A1 | 9/2011 | Pool et al. |
| 2012/0004494 A1* | 1/2012 | Payne et al. ............ 600/9 |
| 2012/0136229 A1 | 5/2012 | Schenberger et al. |
| 2012/0136278 A1 | 5/2012 | Gupta et al. |
| 2012/0232834 A1 | 9/2012 | Roche et al. |
| 2014/0236311 A1 | 8/2014 | Vicatos et al. |

OTHER PUBLICATIONS

Montague, R.G. et al., Servo Control of Magnetic Gears, IEEE/Asme Transactions on Mechatronics, vol. 17, No. 2, pp. 269-278 (Apr. 2012).

International Search Report dated Oct. 21, 2013 PCT/US13/44168 in 3 pages.

* cited by examiner

DEVICES AND METHODS FOR DETECTION OF SLIPPAGE OF MAGNETIC COUPLING IN IMPLANTABLE MEDICAL DEVICES

FIELD OF THE INVENTION

The field of the invention generally relates to implantable medical devices and more particularly, implantable medical devices that undergo changes in length.

BACKGROUND

A variety of medical devices exist that are implanted inside the body and undergo a dimensional change. For example, a bone lengthening device is one type of implantable device that is typically inserted into first and second portions of a severed or broken bone. The device is then periodically lengthened to distract or grow the bone over a period of time. Such adjustments made to the bone lengthening device may be invasive or even non-invasive. As another example, growing rods or distraction devices may be secured to a subject's spine. These devices may be used to correct a medical condition such as scoliosis. In still other applications, these devices may be used to increase the distance between adjacent vertebrae to reduce symptoms associated with lumbar spinal stenosis or pinched nerves. Other bones such as the jaw bone may include an implantable medical device that is configured to elongate over time.

Regardless of the nature in which the implanted medical device is used, there often is a need to determine the length of the implant as it exists inside the patient at any given moment. As an example, after the implanted medical device has undergone a length adjustment there is a need to determine whether or not the desired quantity of lengthening was indeed achieved. U.S. Patent Application Publication No. 2010/0094302 discloses a non-invasive medical implant device that uses microphone sensor on an external adjustment device to sense when an internally-located magnet is undergoing rotation. Specifically, the microphone sensor picks up an acoustic signal (e.g., click) that is periodically generated by rotation of an internal magnet that is part of the implantable medical device. By counting the number of clicks, the external adjustment device can then translate this into an estimated length of the device.

In implanted medical devices that utilize an internally located magnet to effectuate a change in length or force, there sometimes exists the state of "stalled distraction." Stalled distraction refers to the phenomenon that occurs when the implant magnet (i.e., the magnet located within the device implanted inside the body) ceases complete rotations and there is a slipping in the magnetic coupling between the magnetic field(s) of the implant magnet and the externally applied magnetic field(s). This can occur, for example, when the compressive force on the implant drive mechanism exceeds the available distraction force provided by the torque coupling of the externally applied magnetic field (either by an electromagnet or permanent magnet) to the implant magnet. In such instances, while the external magnetic field may be rotating, the internal magnet contained within the implanted device may be prevented from rotating. This may result in inaccurate measurements of the implanted device. For example, the length of the implant may be based on the number of rotations of an externally applied magnetic field which is based on the assumption that the internal magnet rotates in a corresponding manner. If magnetic coupling between the internal magnet and the externally applied magnetic field is interrupted due to slippage, one may not know the actual length of the implant because the internal magnet failed to rotate in accordance with the externally applied magnetic field. The externally applied magnetic field (e.g., five rotations) may lead one to estimate an implant length that is larger than the actual implant length because the internal magnet slipped and failed to rotate in 1:1 correspondence with the externally applied magnetic field (e.g., internally located magnet only rotated three times).

SUMMARY

In one embodiment, a device for the detection of slippage of magnetic coupling between an implanted medical device having a magnet and an externally applied magnetic field includes at least one external magnet configured to apply the externally applied magnetic field, an induction coil disposed external to the subject and between the at least one external magnet and the implanted medical device, and a detection circuit operatively coupled to the induction coil and configured to detect slippage between the rotational orientation of the magnet of the implanted device and the externally applied magnetic field based at least in part on the measured varying frequency components of the voltage waveform across the induction coil.

In another embodiment, a method of detecting slippage of magnetic coupling between an implanted medical device having a magnet and an externally applied magnetic field includes applying a moving external magnetic field to the magnet of the implanted device; interposing an induction coil between the implanted medical device and the externally applied magnetic field; measuring a time varying voltage signal across the induction coil; and detecting slippage of the magnetic coupling based at least in part on detecting a perturbation in the measured time varying voltage signal.

DETAILED DESCRIPTION OF THE ILLUSTRATED EMBODIMENTS

Figure 1:
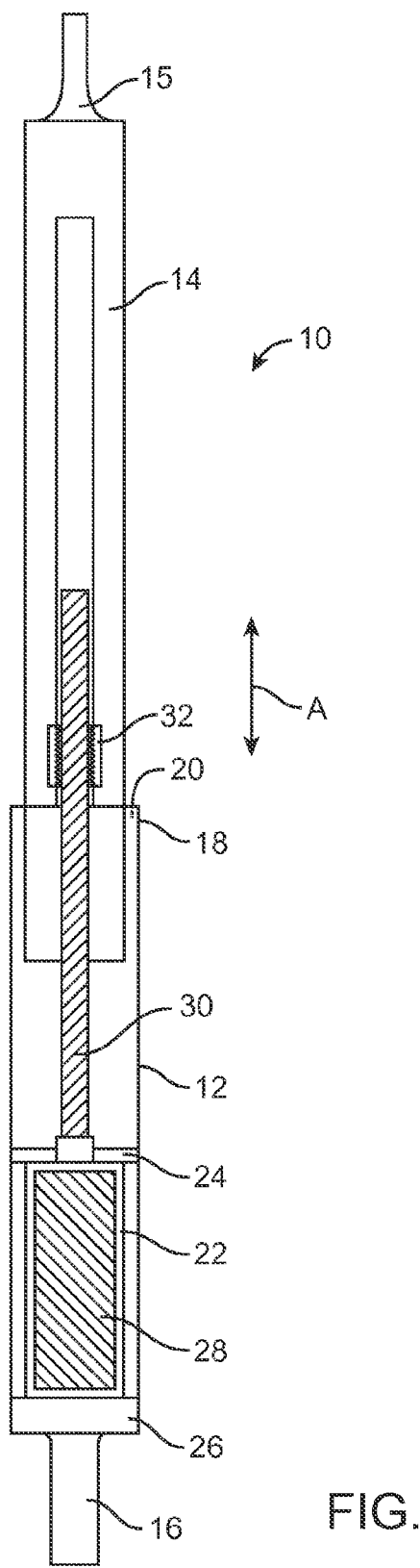
FIG. 1 illustrates an implanted medical device according to one embodiment.

FIG. 1 illustrates an implantable medical device 10 according to one embodiment. The implantable medical device 10 may include a distraction device such as an expandable or growing rod that is implanted inside the body although other implantable medical devices 10 that change in length and/or force are also contemplated. The implantable medical device 10 may be used in various anatomical spaces, for example, including along the spine or within or across other bones of the body. As seen in FIG. 1, the implantable medical device 10 includes a housing 12 and a telescoping rod 14 that moves in a telescoping fashion into and out of the housing 12 in the direction of arrow A. The housing 12 includes a first end 16 that can be secured directly to the anatomical structure using any number of fasteners known to those skilled in the art such as screws, hooks, adhesives, and the like. Likewise, the distal end 15 of the rod 14 can be secured in a similar manner.

A second end 18 of the housing includes a recessed portion 20 in which the telescoping rod 14 is permitted to move in a telescoping fashion. Located inside the housing 12 is a magnetic assembly 22 that is rotationally mounted therein using, for example, respective bearings 24, 26. The magnetic assembly 22 includes a permanent magnet 28 contained therein. The permanent magnet 28 may include, for example, a rare earth magnet formed from, for instance, Neodymium-Iron-Boron. The magnet may be made from a grade of N35 or higher, for example a grade of N50.

The magnetic assembly 22 is secured at one end thereof to a screw 30 that extends longitudinally through the recess 20 of the housing 12 and interfaces with a nut 32 that is contained within the rod 14. Rotation of the magnetic assembly 22 results in corresponding rotation of the screw 30 which, due to the interface between the screw 30 and the nut 32, results in telescopic movement of the rod 14 in the direction of arrow A. Rotational movement in one direction will cause the implantable medical device 10 to lengthen (e.g., distraction) while rotational movement in a second, opposing direction will cause the implantable medical device 10 to shorten (e.g., compression). While FIG. 1 illustrates one particular embodiment of an implantable medical device 10 it should be understood that the particular nature or construction of the implantable medical device 10 may vary considerably. The devices and methods contemplated herein work with any implantable medical device 10 that contains a magnet that is configured for rotation in response to an externally applied moving magnetic field.

Figure 2A:
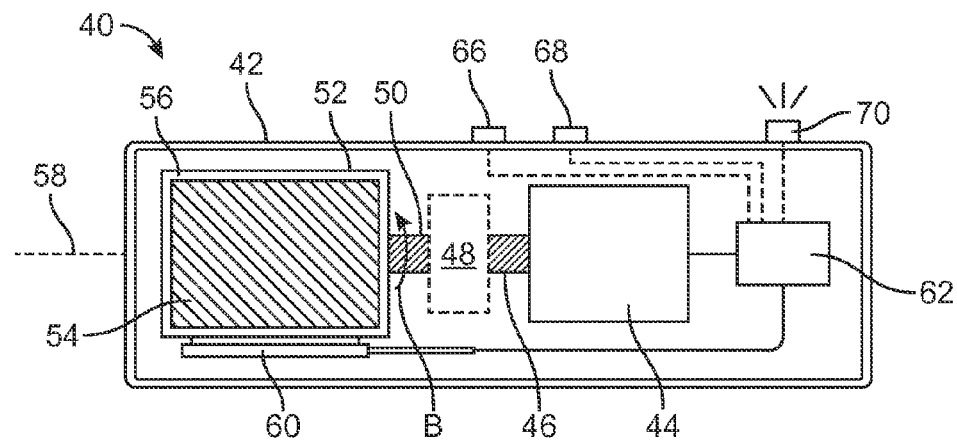
FIG. 2A illustrates an external adjustment device according to one embodiment. The external adjustment device includes a single permanent magnet configured for rotational movement.
Figure 2B:
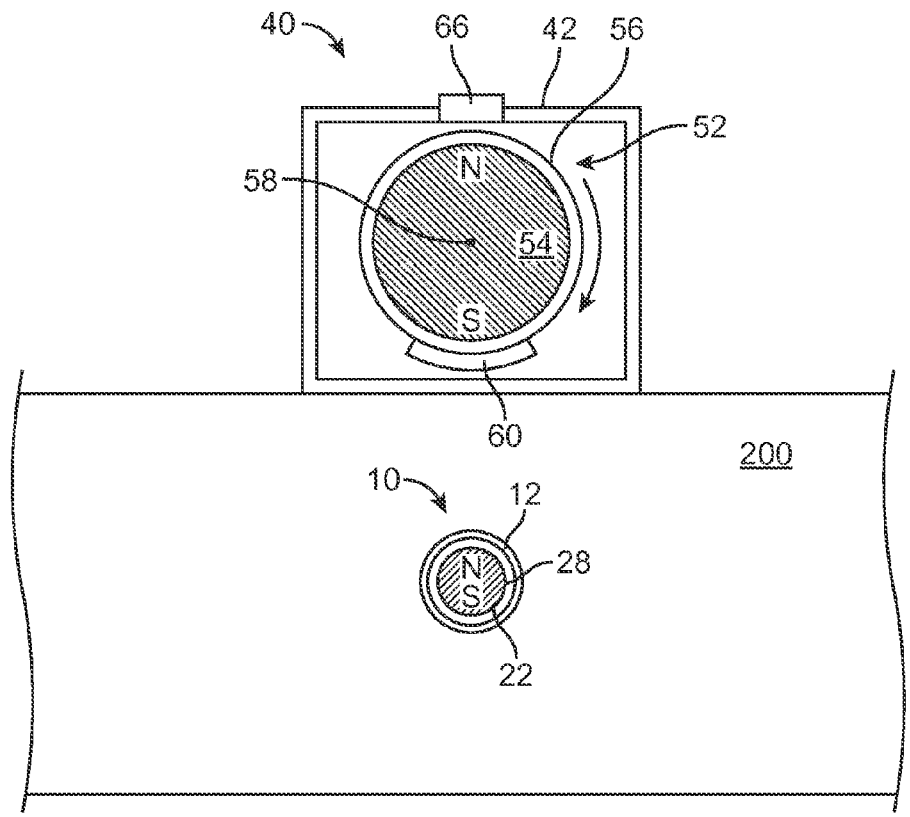
FIG. 2B is a side view of the external adjustment device of FIG. 2A.
Figure 2C:
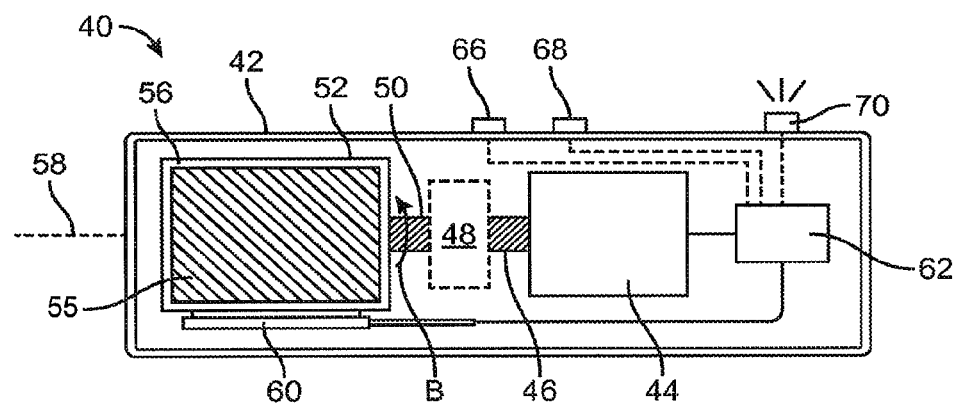
FIG. 2C illustrates an external adjustment device according to one embodiment. The external adjustment device includes a single electromagnet configured to generate a rotating magnetic field.
Figure 2D:
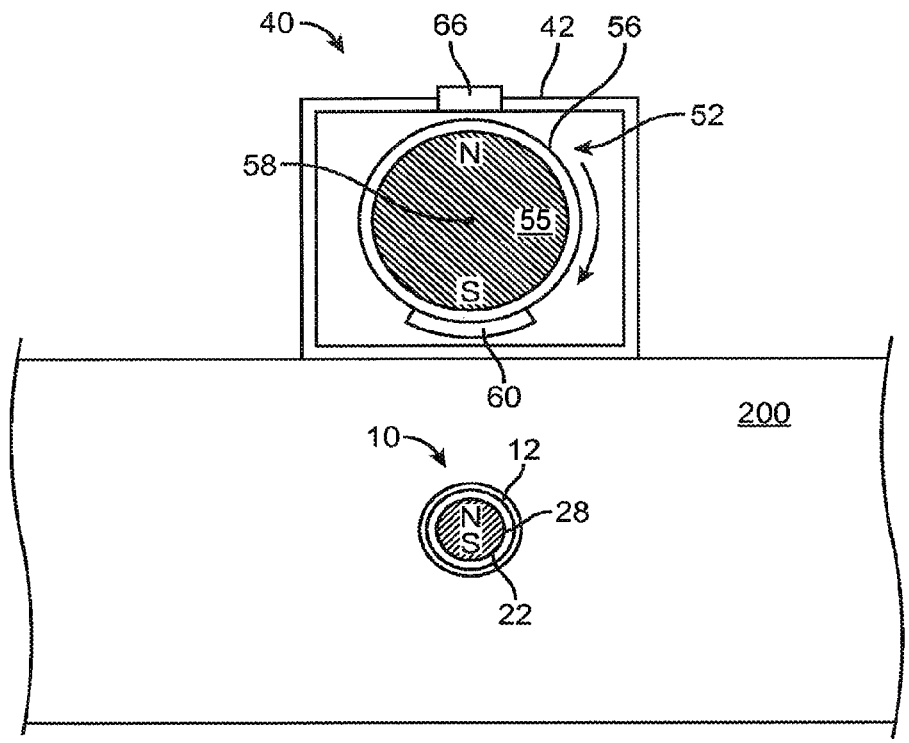
FIG. 2D is a side view of the external adjustment device of FIG. 2C.

FIGS. 2A and 2B illustrate one embodiment of an external adjustment device 40 according to one embodiment. The external adjustment device 40 is used to rotate the magnetic assembly 22 disposed within the implantable medical device 10. In FIG. 2A, the external adjustment device 40 is illustrated as including a housing 42 that contains the various components into an integrated unit. A motor 44 is disposed within the housing 42 and includes an output shaft 46. The output shaft 46 is connected though optional gear(s) 48 to an output shaft 50. In this regard, the output shaft 50 may turn at different rotational speeds as compared to the output shaft 46 of the motor 44. Of course, the gear(s) 48 are optional and it may be possible that no intervening gears are used. The output shaft 46 is coupled to a magnet assembly 52. The magnet assembly 52 includes a permanent magnet 54 that is rotationally mounted within a stationary outer housing 56. The outer housing 56 thus remains stationary while the permanent magnet 54 located therein is able to rotate about a rotational axis 58 (e.g., in the direction of arrow B). In some embodiments, as illustrated in FIGS. 2C and 2D, the magnet assembly 52 includes an electromagnet 55 (rather than a permanent magnet 54) to create a rotating magnetic field.

As seen in FIGS. 2A and 2B, an induction coil 60 is disposed on the outer housing 56 holding the permanent magnet 54. The induction coil 60 may include a wire or other conductor. In one aspect, the induction coil 60 is a coiled wire. The changing magnetic field between the magnetically coupled permanent magnet 28 of the internally-disposed magnetic assembly 22 and the rotating permanent magnet 54 of the external adjustment device 40 induces a current in the induction coil 60 that is proportional to the rate of change of the magnetic field. More specifically, the induced current over the resistance of the induction coil 60 produces a voltage across the length of the conductor or wire that makes up the induction coil 60. This voltage varies with the rate of change of the magnetic field surrounding the induction coil 60. As explained below, the time-varying voltage is the signal that can be monitored to detect slippage between the permanent magnet 28 of the implantable medical device 10 and the permanent magnet 54 of the external adjustment device 40.

The external adjustment device 40 includes circuitry 62 (e.g., detection circuitry) that is used to monitor the time varying voltage signal in the induction coil 60. This same circuitry 62 may also be used, optionally, to control the motor 44. For example, the circuitry 62 may interface with inputs 66, 68 (e.g., buttons) that drive the motor 44 in opposing directions. Alternatively, the circuitry 62 may receive instructions input from the user on the desired degree of change of length of the implantable medical device 10 (e.g., distract 1 mm). The circuitry 62 may be integrated into one or more processors or the like that is located within the external adjustment device 40. The electronics for the circuitry 62 and the motor 44 may be supplied using a cable the plugs into a standard A/C wall outlet or it may be powered by one or more batteries contained in the external adjustment device 40.

As explained herein in more detail, the circuitry 62 is used to detect slippage of magnetic coupling between the permanent magnet 28 of the implantable device 10 and the permanent magnet 54 of the external adjustment device 40. The circuitry 62 monitors the time varying voltage signal from the induction coil 60 and looks for perturbations in this signal. Perturbations or "twitches" of the voltage signal are, as explained below, are indicative that slippage between the permanent magnet 28 of the implantable device 10 and the permanent magnet 54 of the external adjustment device 40. As the permanent magnet 54 of the external adjustment device 40 rotates, the permanent magnet 28 of the implantable device 10 will also rotate provided that the permanent magnet 28 of the implantable device 10 is not restricted from rotational movement. If, however, the permanent magnet 28 of the implantable device 10 is restricted from movement and the permanent magnet 54 of the external adjustment device 40 rotates, one can define a "lagging angle" as the angle through which the permanent magnet 28 of the implantable device 10 would have rotated but for the restriction. When the lagging angle between the coupled magnetic fields increases beyond 180°, the permanent magnet 28 of the implantable device 10 accelerates and then decelerates through this lagging angle and results in a "twitch." The twitch is detected by the circuitry 62 which indicates slippage between the two respective magnetic fields.

In vivo, rotating the permanent magnet 28 in the distraction direction increases the torque required to rotate it further in that direction. Conversely, rotating the permanent magnet 28 in the retraction direction reduces the torque required to then rotate it in the distraction direction (assuming device is not in tension yet). If the permanent magnet 28 stalls during distraction, when the lagging angle reaches 180° the permanent magnet 28 will reverse direction and twitch until the fields align, distraction torque is applied, and the permanent magnet 28 again rotates in the distraction direction with increasing torque as the lagging angle increases.

The magnetic field orientations of the coupled magnets 28, 54 rotate through a cycle. The cycle repeats with every rotation of the permanent magnet 54 of the external adjustment device 40. The scalar amount of torque imparted by the coupled fields on the permanent magnet 28 rises and falls on the same cycle. If at some point the permanent magnet 28 stalls, the permanent magnet 28 will twitch with every subsequent magnet 54 rotation cycle until the distraction force is lowered.

The changing magnetic field or perturbation caused by the twitch is sensed by the induction coil 60. The changing magnetic field induces a current in the conductor or wire of the induction coil 60. A 90° rotation of the permanent magnet 28 over 6 milliseconds produces a change in the coupled magnetic field large enough to be detected with the required discretion to be a reliable indication of stalled distraction. The induced current over the resistance in the conductor or wire of the induction coil 60 produces a voltage potential across the length of conductor or wire in the induction coil 60. This voltage varies with the rate of change of the magnetic field surrounding the induction coil 60. It is this time varying voltage that is the signal from which the twitch can be identified.

As best seen in FIG. 2A, the external adjustment device 40 includes an indicator 70 that is operatively coupled to circuitry 62. The indicator 70 alerts the user of the external adjustment device 40 to slippage of magnetic coupling. This indictor 70 may include a visual indicator such as illumination of a light or LED. The indicator 70 may also include an audible indicator that emits a tone or other sound to indicate slippage. As yet another alternative, the indicator 70 may include a tactile indicator that vibrates or otherwise causes movement that may be sensed by the user holding the external adjustment device 40. A piezoelectric-based vibrating element may, for example, be used.

Figure 3:
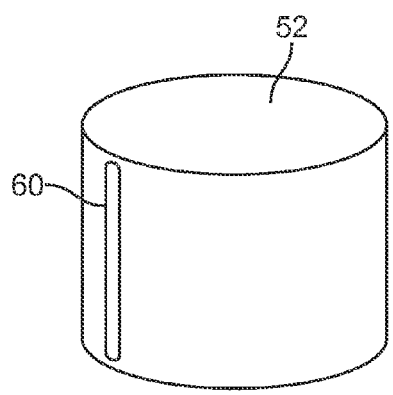
FIG. 3 illustrates a magnet assembly containing a permanent magnet therein. An induction coil is disposed adjacent to the magnet assembly.

FIG. 3 illustrates the magnet assembly 52 of the external adjustment device 40 with an oval-shaped induction coil 60 in the shape of a coil. As explained above, the induction coil 60 may be mounted on the surface of the magnet assembly 52 or it can be mounted elsewhere in or on the external adjustment device 40 such that the induction coil 60 is interposed and stationary between the permanent magnet 28 of the implantable medical device 10 and the permanent magnet 54 of the external adjustment device 40. The induction coil 60 does not need to lie in a plane between the permanent magnet 28 and the permanent magnet 54 of the external adjustment device 40. The induction coil 60 may, for example, be laterally offset from a plane or line connecting permanent magnet 28 to permanent magnet 54. In addition, there may be some degree of overlap between the outer periphery of the permanent magnets 28, 54 and the induction coil 60. Likewise, the induction coil 60 does not have to be coil-shaped as any shape will respond to changes in the magnetic field.

Figure 4:
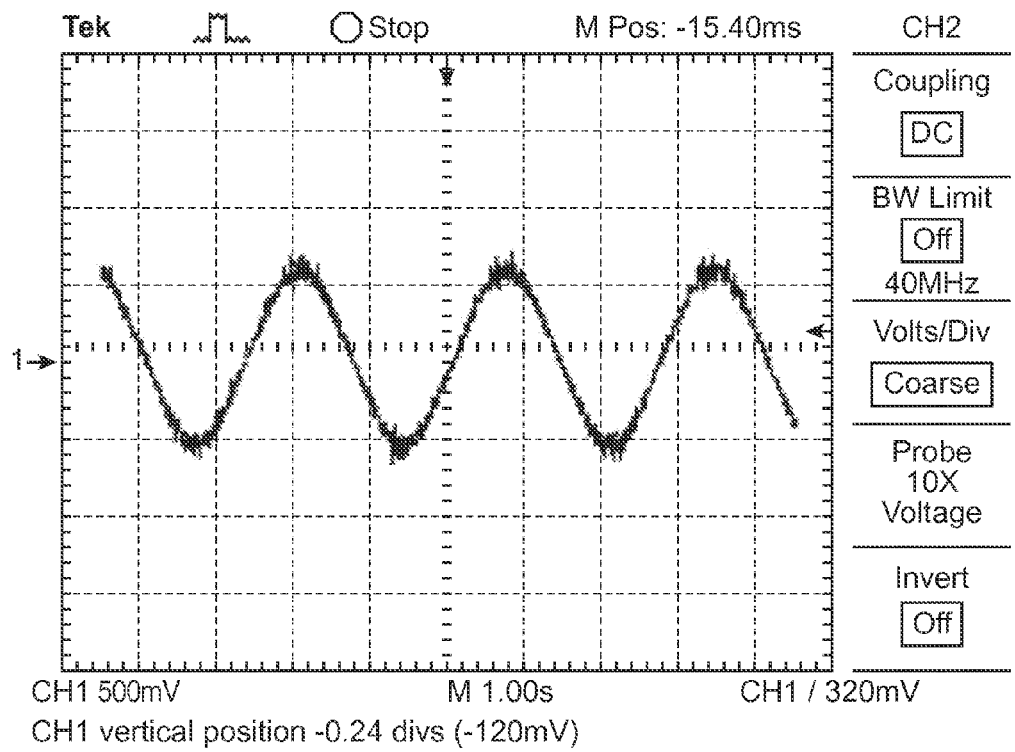
FIG. 4 is graph of the signal captured by the induction coil on the external adjustment device of FIGS. 2A and 2B. The induction coil was a forty (40) turn coil. The illustrated signal is amplified 100×.

During use, the external adjustment device 40 is brought in close proximity to the subject 200 as seen in FIG. 2B whereby the permanent magnet 54 of the external adjustment device 40 is actuated. The rotational speed of the permanent magnet 54 of the external adjustment device 40 may vary but it is generally around 30 rpm (a period of 0.5 Hz). Rotation of the magnetic field of the permanent magnet 54 of the magnet assembly 52 induces a time varying voltage across the induction coil 60 that approximates a sinusoid. As an example, a one inch diameter, 40 turn coiled induction coil 60, which is reoriented into the shape shown in FIG. 3 produces a 10 mV peak to peak cyclic signal when mounted 4 mm from the surface of a two inch diameter×1.5" long permanent magnet 54 as seen in FIG. 4. Different permanent magnets 54 (different in dimension or bulk magnetization) would induce different signals in the induction coil 60 (both shape and amplitude) depending on the change in the strength and direction of the magnetic field vector acting on the induction coil 60 as the permanent magnet 54 rotates.

Figure 5:
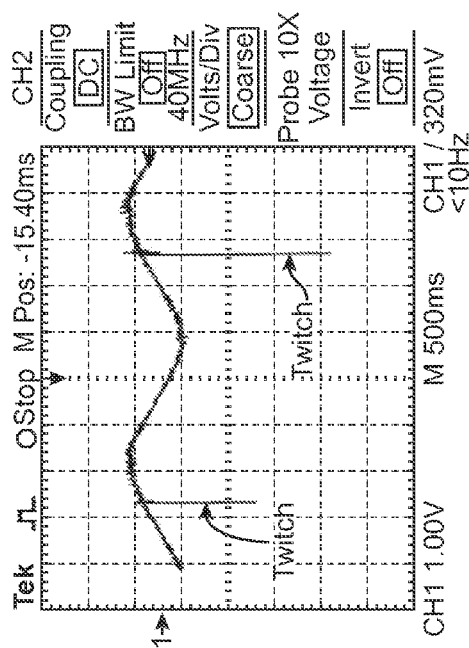
FIG. 5 is a graph of the perturbation or twitch signal superimposed on the signal of the external adjustment device captured by the induction coil.

FIG. 5 illustrates a similar sinusoidal signal obtained from an induction coil 60 interposed between a rotating permanent magnet 54 and a permanent magnet 28 of the implantable medical device 10. However, unlike FIG. 4, in this illustration, the permanent magnet 28 is stalled and a twitch signal is produced and captured by the induction coil 60. The twitch signals are shown superimposed on the sinusoidal signal of the rotating permanent magnet 54 in FIG. 5. The shape and amplitude of the twitches will vary depending on the relative alignment of the fields at the time of the stall. Generally, the frequency of the twitch signal is between about 150 Hz and about 200 Hz (e.g., ~170 Hz) which is high enough relative to the signal produced by the magnet of the permanent magnet 54 of the external adjustment device 40 such that it can be separated by passive networks, rectified, and normalized using a comparator as part of circuitry 62. The resultant signal can be used to trigger an alert to the user via indicator 70 as notification that the stall has been detected. In another embodiment, detection of one or more twitches may automatically prevent additional rotations of the permanent magnet 54 of the external adjustment device 40, for example by control circuitry stopping a motor that control rotation of the permanent magnet 54.

Figure 6:
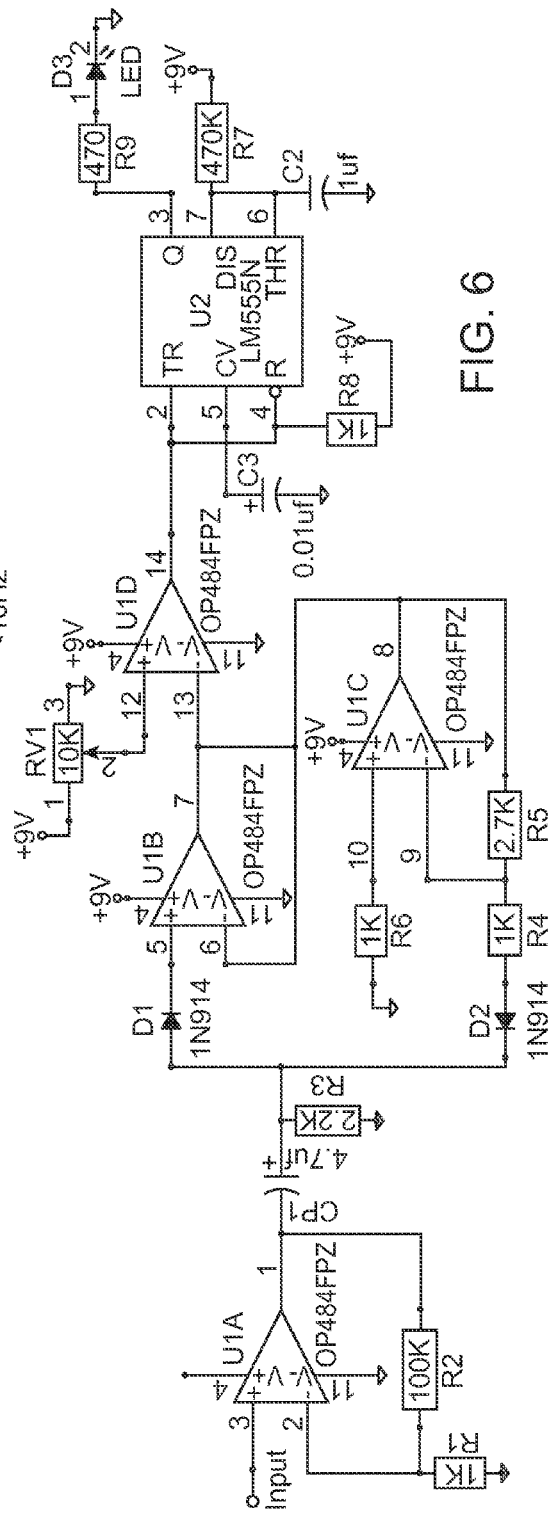
FIG. 6 is a perturbation or twitch detection circuit for the external adjustment device of FIGS. 2A and 2B.

A circuit suitable to accomplish this detection is shown in FIG. 6. Op-amp U1A provides an initial voltage gain of 100. Capacitor CP1 and resistor R3 form a passive high pass filter with a 3 db cut off frequency of ~15 Hz. This removes the 0.5 Hz sinusoidal component (generated by external adjustment device 40) from the waveform. Op-amps U1B and U1C (with diodes D1 and D2) rectify the waveform such that all voltages are positive. FIG. 5 shows that there are instances when the highest angular velocity of the twitch is in the direction that produces a negative potential. Rectifying the waveform ensures that the largest angular velocity component of the twitch is utilized in the detection. Op-amp U1D is a comparator whose reference is set by variable resistor RV1. The reference is set at ~2× the amplitude of noise in the waveform. This eliminates false positive trigger events. The output of op-amp U1D is the positive rail voltage for the duration that the twitch potential is above the reference. The output of op-amp U1D provides the trigger pulse to integrated circuit U2, a 555 timer configured as a mono-stable tank circuit. Timing components capacitor C3 and resistor R8 determine that the light emitting diode LED D3 will light for ~0.3 seconds when a trigger pulse is sensed.

Figure 7A:
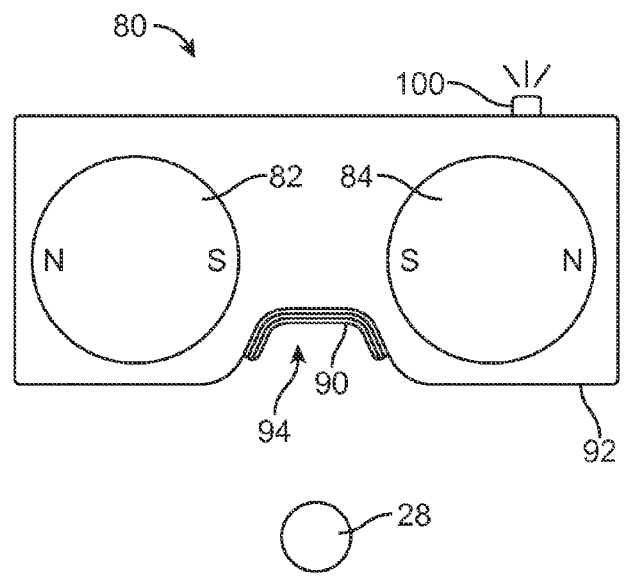
FIG. 7A illustrates a side view of an external adjustment device according to another embodiment.
Figure 7B:
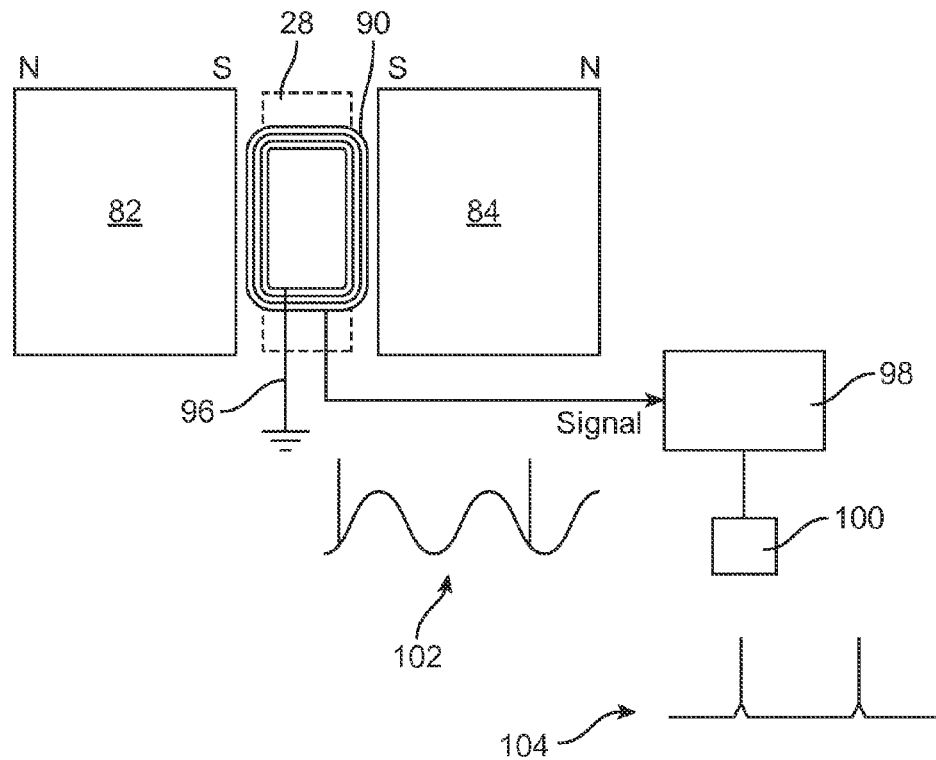
FIG. 7B illustrates a bottom view of the external adjustment device of FIG. 7A.
Figure 7C:
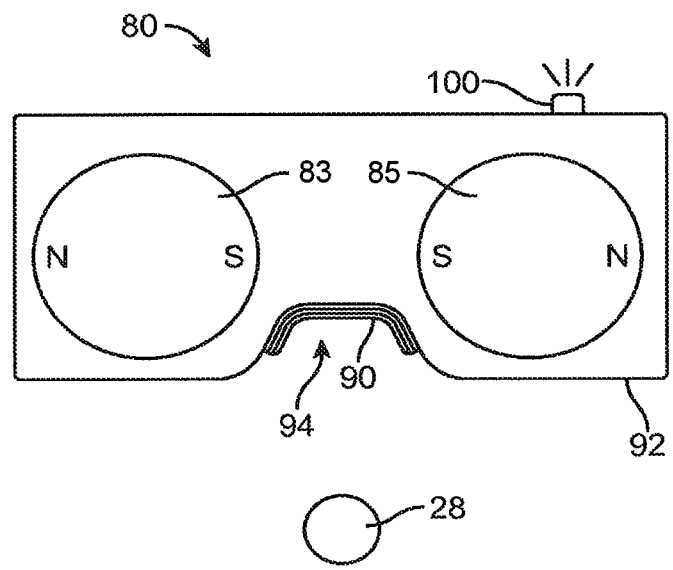
FIG. 7C illustrates a side view of an external adjustment device according to another embodiment.
Figure 7D:
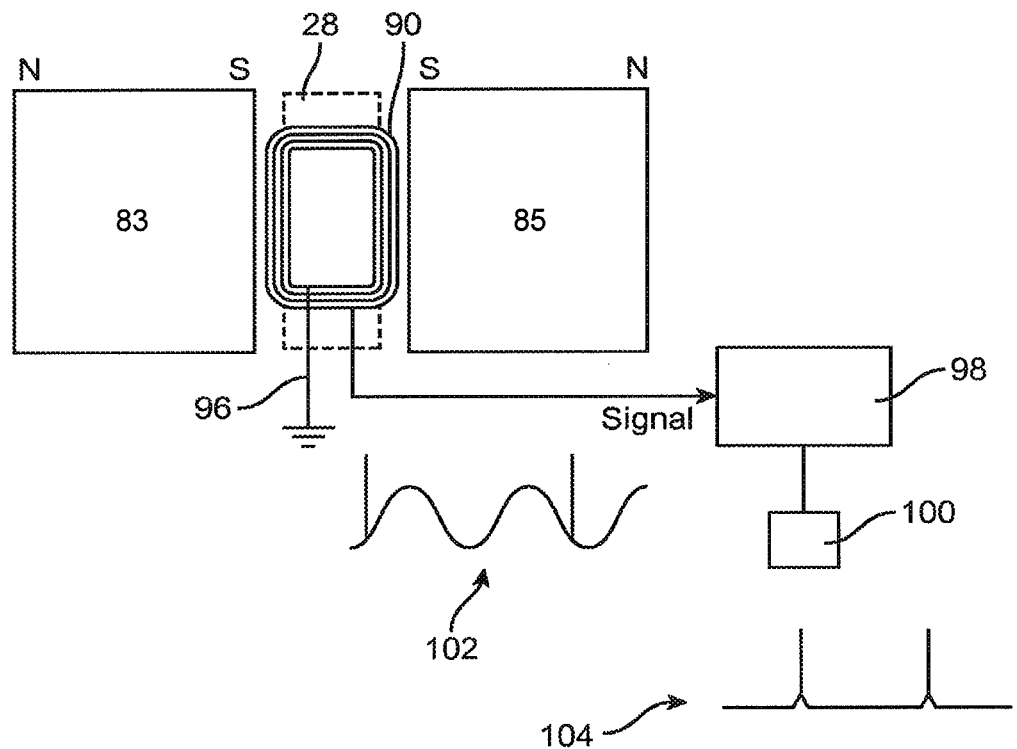
FIG. 7D illustrates a bottom view of the external adjustment device of FIG. 7C.
Figure 8:
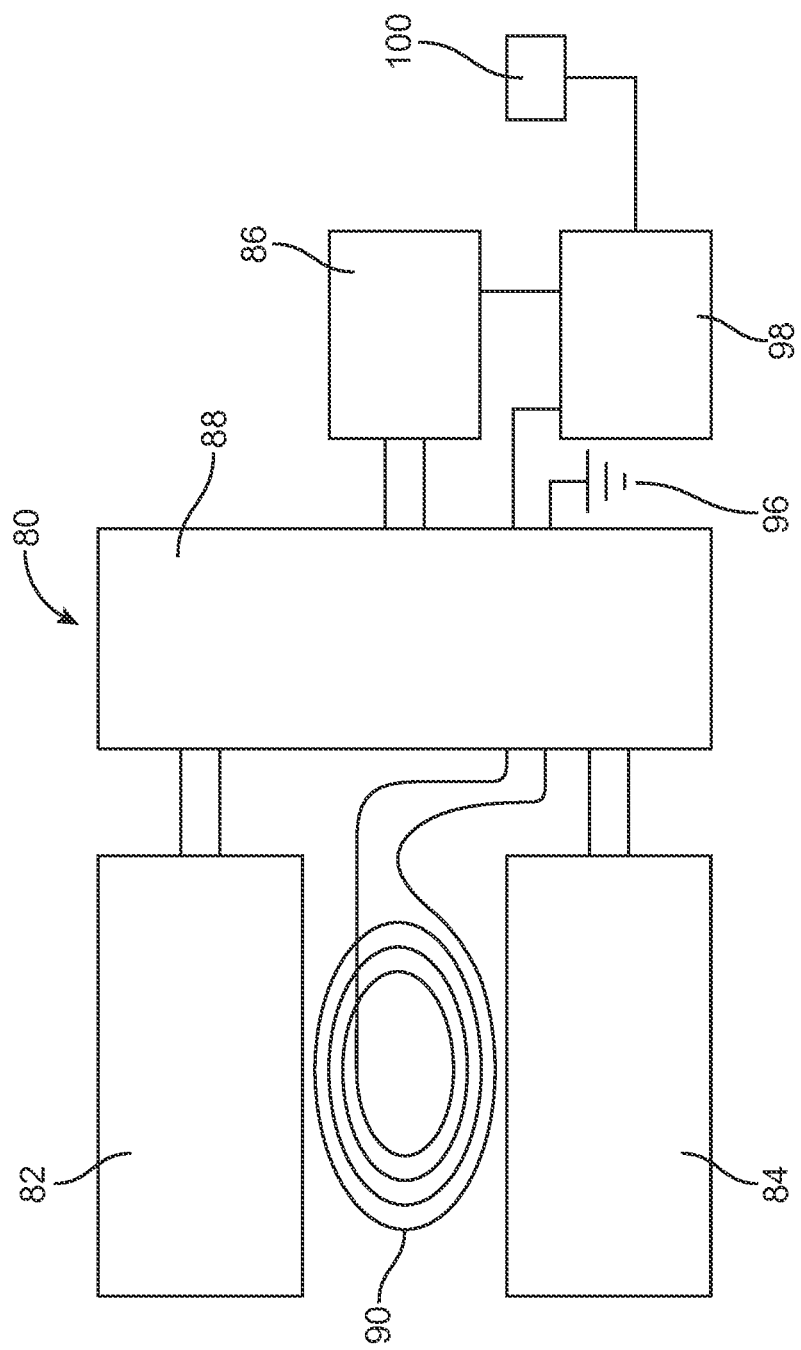
FIG. 8 schematically represents a two magnet external adjustment device.
Figure 8A:
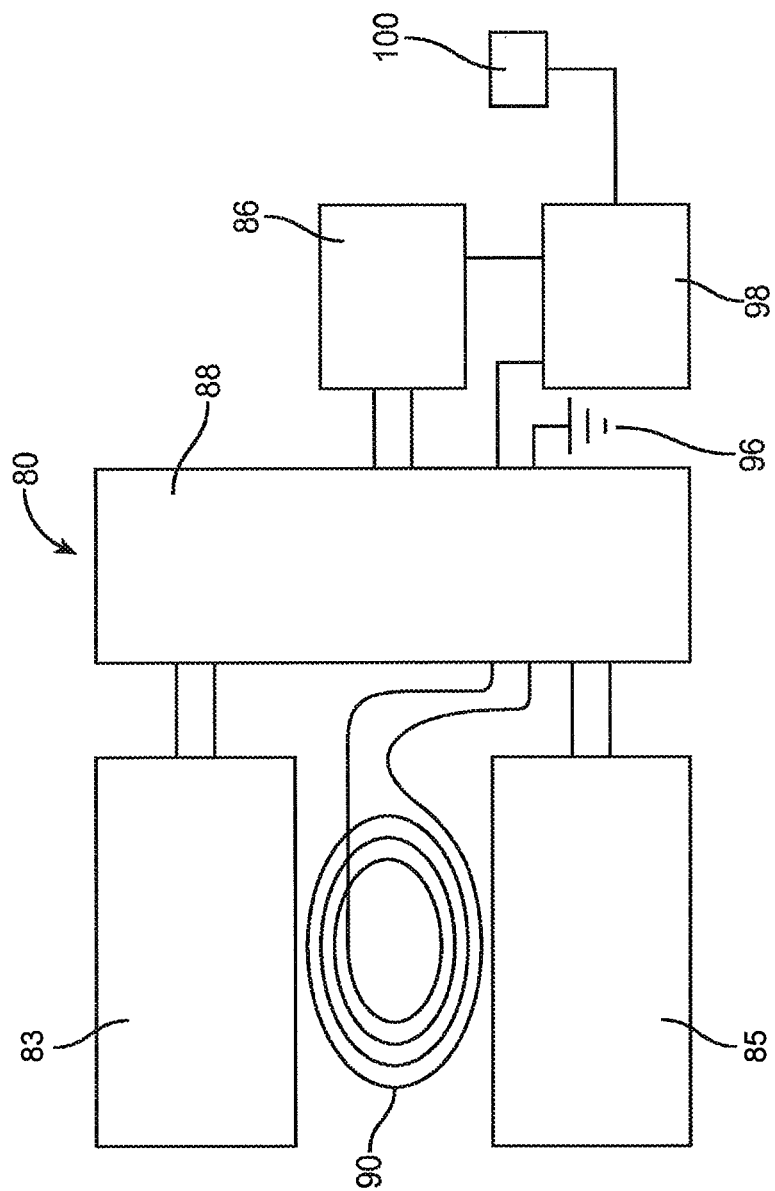
FIG. 8A schematically represents an external adjustment device having two electromagnets.

FIGS. 7A, 7B, 7C, 7D, 8, and 8A illustrate alternative embodiments of an external adjustment device 80. This external adjustment device 80 is different from the external adjustment device of FIGS. 2A, 2B, 2C, and 2D in that there are two (2) permanent magnets 82, 84, or electromagnets 83, 85, whose magnetic fields, or, in the case of electromagnets 83 and 85, the magnetic fields they create, are aligned and rotate in synchronization. The two (2) permanent magnets are 82, 84 are positioned close enough such that their respective magnetic fields cycle through attraction and repulsion. As seen in FIG. 8, both permanent magnets 82, 84 are driven using a motor 86 that couples to each permanent magnet 82, 84 via gearing 88. Examples of external adjustment devices having two permanent magnets and usable in connection with the devices and methods disclosed herein include those disclosed in U.S. Pat. No. 7,862,502, U.S. Patent Application Nos. 2010-0217271 and 2012-0004494, which are incorporated herein by reference. An induction coil 90 is disposed between each permanent magnet 82, 84. The induction coil 90 may include a coil, loop, or other structure as described herein and may be mounted on or within a housing 92 forming the external adjustment device 80. As best seen in FIG. 7A, the induction coil 90 may have an arcuate shape that conforms to the recess 94 formed in the housing 92 between permanent magnets 82, 84.

The induction coil 90 is coupled to ground 96 at one end (as seen in FIGS. 7B and 8) while the opposing end of the induction coil is coupled to circuitry 98 where the time varying voltage signal is monitored as explained herein. The circuitry 98 may also optionally interface with the motor 86 so as to control the rotation of the permanent magnets 82, 84. The circuitry 98 is connected to an indicator 100 that is similar to the indicator 70 described with the respect to the prior embodiment. In this regard, the indicator 100 may alert a user of the external adjustment device 80 to slippage of the permanent magnet 28 of the implantable device 10 using a visual, auditory, or tactile/haptic signal. FIG. 7B illustrates the oscillating raw signal 102 received by the induction coil 90. This signal 102 is then processed and monitored by circuitry 98 in which the higher frequency twitches are passed and rectified (seen as signal 104) which is used to trigger an alert at indicator 100.

Figure 9:
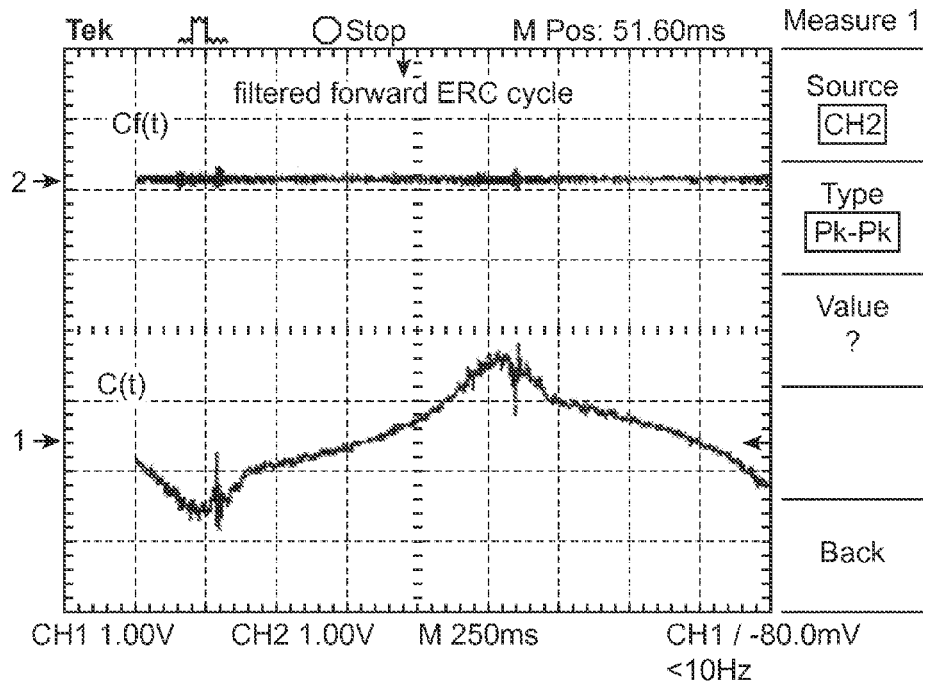
FIG. 9 is a graph of the signal of a two magnet external adjustment device captured by an induction coil. The induction coil is a coil having 20 turns and the signal is amplified 23×.

The permanent magnets 82, 84 of the external adjustment device 80 are connected with gearing 88 (e.g., multiple gears) that have some level of lash. This allows for the production of an external adjustment device 80 twitch in the same way that the permanent magnet 28 of the implantable medical device 10 (i.e., driven magnet) twitches are produced, however, these may be removed by the circuitry 98 during processing of the signal. Additionally, the strong magnetic coupling of the permanent magnets 82, 84 of the external adjustment device 80 adds higher order components to the base external adjustment device 80 waveform produced by the induction coil 90 (as seen in FIG. 9). The lower trace in FIG. 9 (C(t)) shows the signal from a 20 turn, one inch diameter pickup coil induction coil 90 mounted to a dual magnet external adjustment device 80 as shown in FIGS. 7A and 7B. The higher frequency components are the magnet twitch of the external adjustment device 80. The wavelength of these components was measured to be ~50 Hz—100× the frequency of the single magnet external adjustment device 40 from the embodiment illustrated in FIGS. 2A and 2B. The complete waveform with the driven magnet twitch is illustrated in the upper trace FIG. 10.

Figure 11:
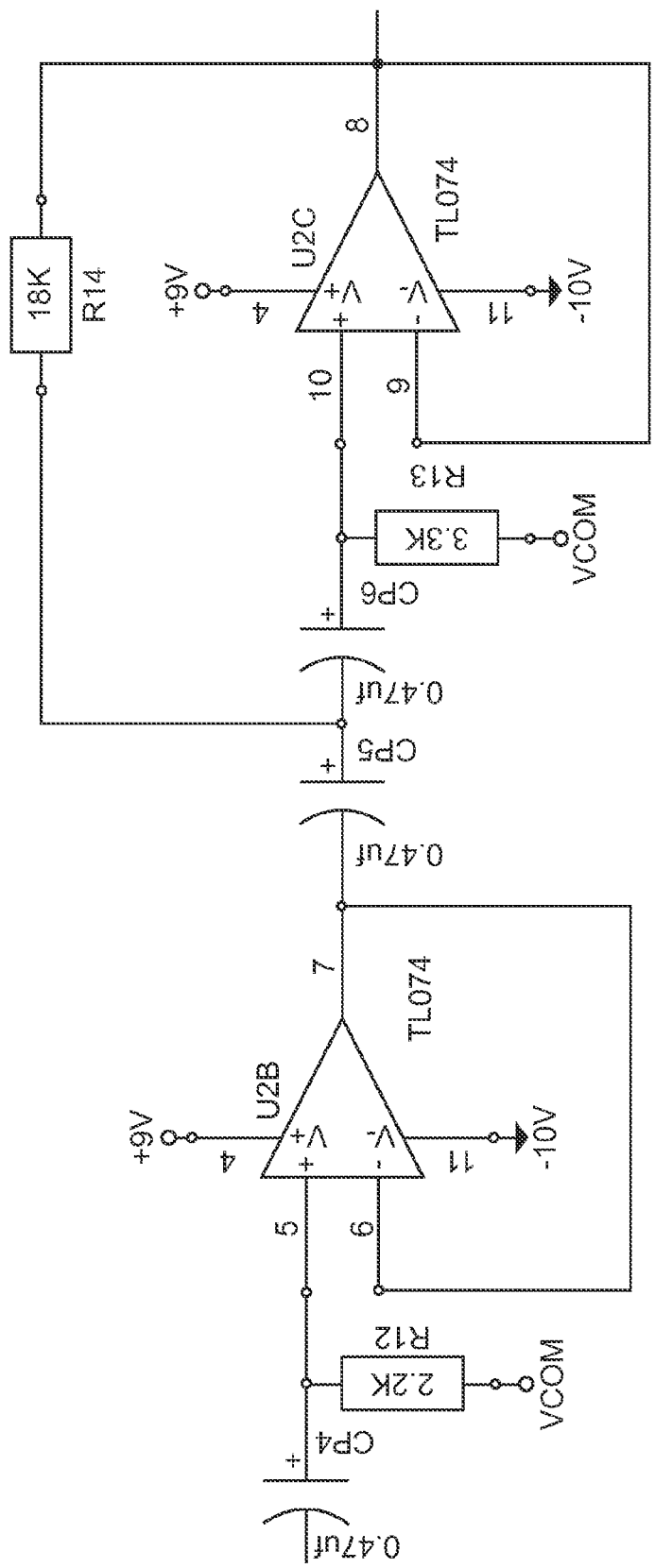
FIG. 11 is a schematic of a $3^{rd}$ order Bessel filter circuit ($f_c$~200 Hz) used to form an active filter network.

The circuitry 98 includes an active filter network that is used to separate the ~150-200 Hz twitch signal from the driven magnet 28 from the base waveform produced by the external adjustment device 80 so that the twitch of the permanent magnet 28 of the implantable medical device 10 is not masked by the twitch caused by the attraction of the permanent magnets 82, 84 of the external adjustment device 80 to each other. A third order Bessel filter was developed for this purpose and is illustrated in FIG. 11. As seen in FIG. 11, the circuit components include op-amps U2B, U2C; resistors R12, R13, R14; and capacitors CP4, CP5, and CP6. The frequency response of the filter was measured at the two (2) points of interest as shown below in Table 1.

TABLE 1

| Frequency [=] Hz | Output V [=] V |
|---|---|
| 50 | 0.26 |
| 170 | 2.64 |

The data in Table 1 indicates that there would be a 10 db attenuation of the magnet twitch of the external adjustment device 80 relative to the twitch of the permanent magnet 28 of the implantable medical device 10. This is enough discretion to allow reliable detection of the magnet twitch of the permanent magnet 28 of the implantable medical device 10.

$dbV_{50/170} = 10 \log(0.26/2.64) = -10$

Figure 10:
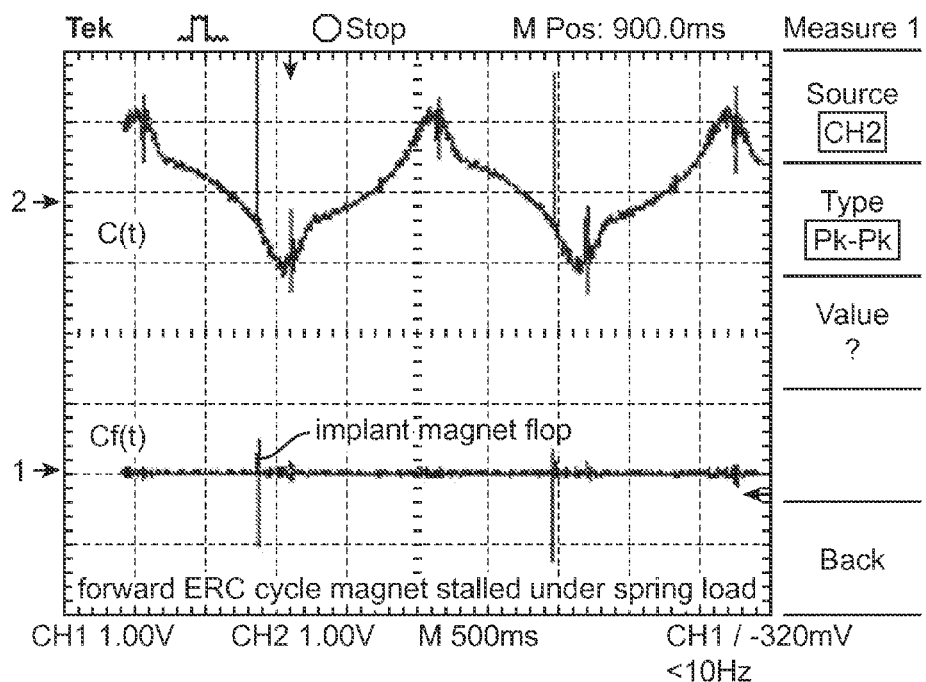
FIG. 10 is a graph of the perturbation or twitch signal superimposed on the signal (complete waveform) of a two magnet external adjustment device captured by the induction coil.
Figure 12:
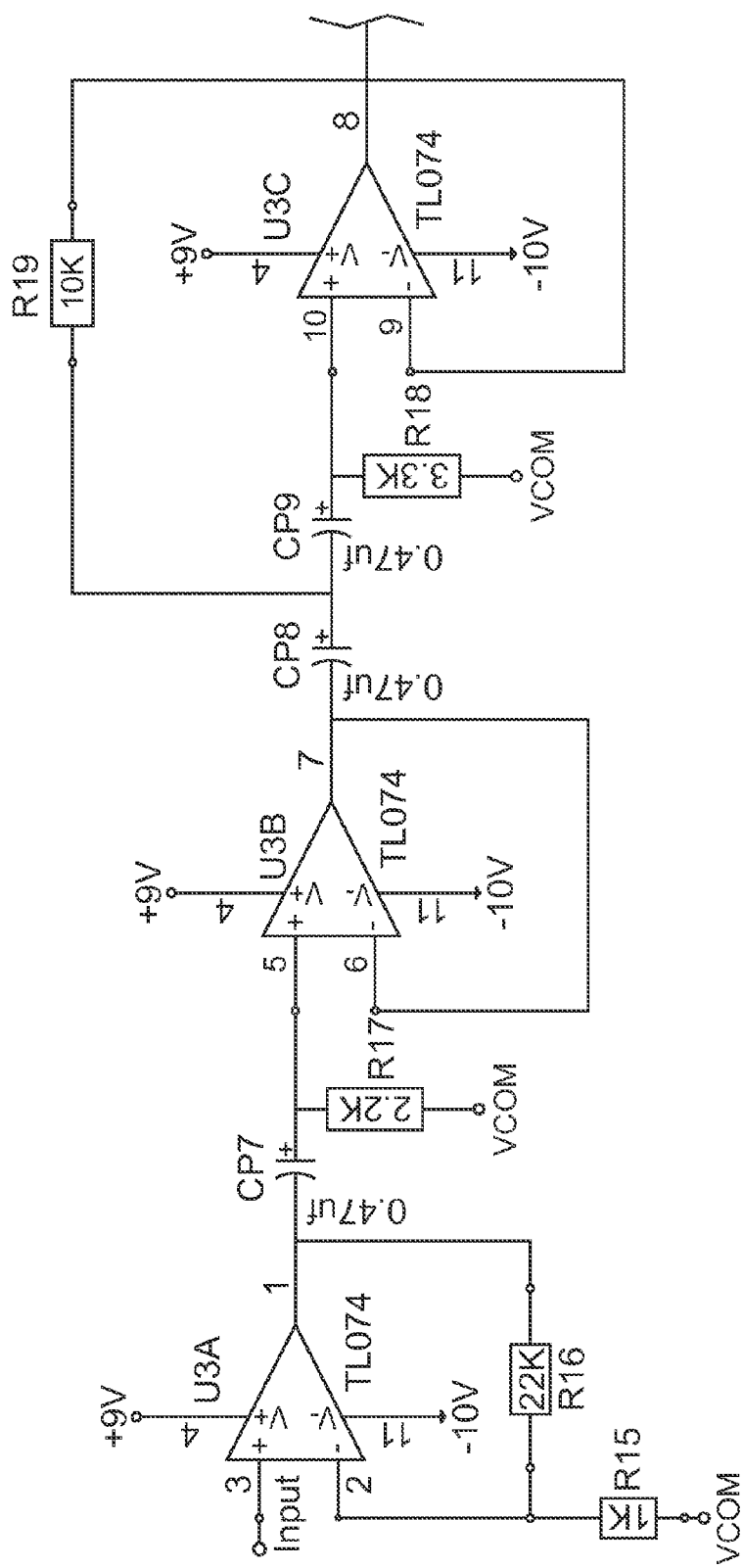
FIG. 12 is a schematic of a circuit for twitch detection for the dual magnet embodiment of FIGS. 7A and 7B with a visual alert indicator.
Figure 12:
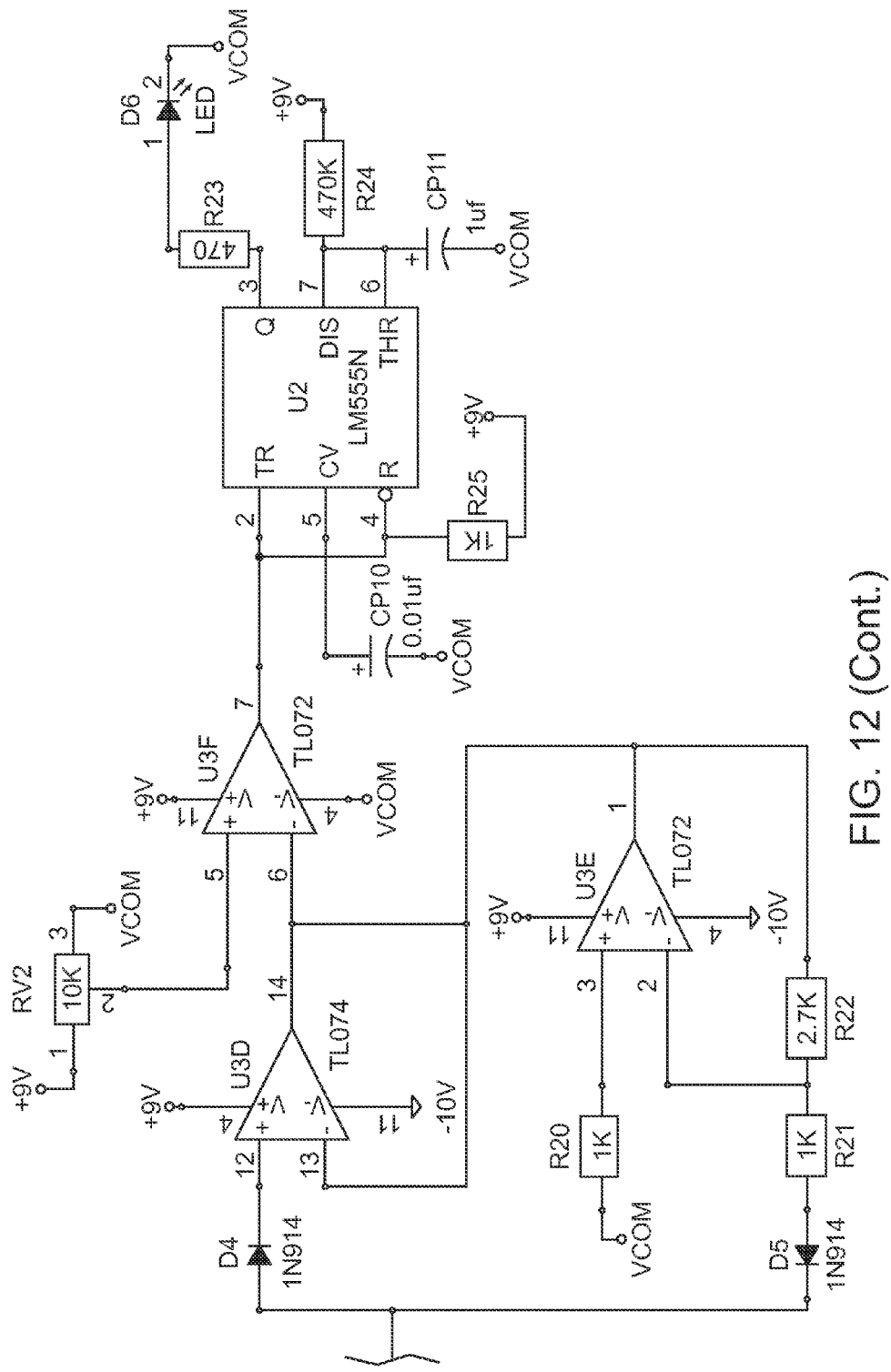

The filtered waveform is shown as the lower trace in FIG. 10. This waveform can be rectified and normalized using a comparator as in the embodiment of FIGS. 2A and 2B. The resultant signal can be used to trigger an alert indicator 100 as notification that the stall has been detected. Circuitry 98 suitable to accomplish this detection is shown in FIG. 12. Op-amp U3A provides an initial voltage gain of 23. Capacitor CP7 and resistor R17 and op-amps U3B and U3C form the active filter of FIG. 11. This removes the <50 Hz components of the external adjustment device 80 from the waveform. Op-amps U3D and U3E (with diodes D4 and D5) rectify the waveform such that all voltages are positive. FIG. 10 shows that there are instances when the highest angular velocity of the twitch is in the direction that produces a negative potential. Rectifying the waveform ensures that the largest angular velocity component of the twitch is utilized in the detection. Op-amp U3F is a comparator whose reference is set by variable resistor RV2. The reference is set at ~2× the amplitude of noise in the waveform. This eliminates false positive trigger events. The output of op-amp U3F is the positive rail voltage for the duration that the twitch potential is above the reference. The output of op-amp U3F provides the trigger pulse to integrated circuit U3, a 555 timer configured as a mono-stable tank circuit. Timing components including capacitor CP10 and resistor R25 determine that the LED D6 will lite for ~0.3 seconds when a trigger pulse is sensed.

While embodiments have been shown and described, various modifications may be made without departing from the scope of the inventive concepts disclosed herein. For example, while the embodiments described herein have used permanent magnets in the external adjustment device 40, 80 it should be understood that permanent magnets may be replaced with electromagnets. Also, the circuits illustrated in FIGS. 6, 11, and 12 are exemplary and other circuit configurations may also be used. The invention(s), therefore, should not be limited, except to the following claims, and their equivalents.

What is claimed is:

1. A device for the detection of slippage of magnetic coupling between an implanted medical device having an implanted magnet and an externally applied magnetic field comprising:
   at least one external magnet configured to apply the externally applied magnetic field;
   a coiled wire disposed external to a subject and between the at least one external magnet and the implanted medical device, wherein the coiled wire is configured to generate a time varying voltage in response to a changing magnetic field, wherein a magnitude of the time varying voltage is proportional to a rate of change of the changing magnetic field; and
   a detection circuit configured to detect a twitch signal comprising at least one varying frequency component of the time varying voltage, wherein the at least one varying frequency component is indicative of slippage between a magnetic field of the implanted magnet and the externally applied magnetic field.

2. The device of claim 1, wherein the at least one external magnet comprises an electromagnet.

3. The device of claim 1, wherein the detection circuit comprises a high pass filter.

4. The device of claim 1, wherein the at least one external magnet comprises a permanent magnet.

5. The device of claim 1, wherein the at least one external magnet comprises two spaced apart permanent magnets.

6. The device of claim 5, wherein the coiled wire is disposed between the two spaced apart permanent magnets.

7. The device of claim 1, wherein the at least one varying frequency component of the time varying voltage comprises frequencies within the range of about 150 Hz to about 200 Hz.

8. The device of claim 1, further comprising an operator alert operatively coupled to the detection circuit.

9. The device of claim 8, wherein the operator alert comprises one of a visual indicator, an audible indicator, and a tactile indicator.

10. A method of detecting slippage of magnetic coupling between an implanted medical device having an implanted magnet and an externally applied magnetic field comprising:
    applying a moving external magnetic field to the implanted magnet;
    interposing a coiled wire between the implanted medical device and the externally applied magnetic field;
    measuring a time varying voltage signal across the induction coil; and
    detecting a twitch signal comprising at least one varying frequency component of the time varying voltage signal, wherein the at least one varying frequency component is indicative of slippage of the magnetic coupling.

11. The method of claim 10, wherein the moving external magnetic field is applied by a permanent magnet.

12. The method of claim 10, wherein the moving external magnetic field is applied by an electromagnet.

13. The method of claim 10, wherein the time varying voltage signal is filtered.

14. The method of claim 13, wherein the time varying voltage signal is rectified.

15. The method of claim 10, further comprising initiating an alert upon detection of the twitch signal.

16. The method of claim 15, wherein the alert comprises one of a visual, audible, or tactile alert.

17. The method of claim 10, further comprising stopping the moving external magnetic field upon detection of the twitch signal.

18. The method of claim 17, wherein the moving external magnetic field is automatically stopped by a control circuitry.

19. The method of claim 17, wherein the twitch signal comprises a signal with a frequency within the range of about 150 Hz to about 200 Hz.

* * * * *